(12) United States Patent
Kadziauskas et al.

(10) Patent No.: US 6,733,491 B2
(45) Date of Patent: May 11, 2004

(54) CATARACT EXTRACTION APPARATUS AND METHOD

(75) Inventors: Kenneth E. Kadziauskas, Coto de Caza, CA (US); Mark E. Steen, Chino Hills, CA (US)

(73) Assignee: Advanced Medical Optics, Santa Ana, CA (US)

( * ) Notice: Subject to any disclaimer, the term of this patent is extended or adjusted under 35 U.S.C. 154(b) by 30 days.

(21) Appl. No.: 09/949,405

(22) Filed: Sep. 7, 2001

(65) Prior Publication Data

US 2003/0050629 A1 Mar. 13, 2003

(51) Int. Cl.[7] .................. A61B 18/18; A61B 17/20; A61N 5/00
(52) U.S. Cl. .................. 606/6; 606/4; 607/88; 607/89; 604/21; 604/22
(58) Field of Search .................. 606/4–6, 13–16, 606/32, 41; 607/88, 89, 96–105, 115, 116

(56) References Cited

U.S. PATENT DOCUMENTS

| | | | | | |
|---|---|---|---|---|---|
| 4,744,360 A | * | 5/1988 | Bath | ..................... | 128/303.1 |
| 5,057,098 A | * | 10/1991 | Zelman | ..................... | 606/6 |
| 5,123,902 A | * | 6/1992 | Muller et al. | ............. | 604/21 |
| 5,403,307 A | * | 4/1995 | Zelman | ..................... | 606/6 |
| 5,738,677 A | * | 4/1998 | Colvard et al. | ............ | 606/4 |
| 6,013,049 A | * | 1/2000 | Rockley et al. | ........... | 604/22 |
| 6,083,193 A | * | 7/2000 | Kadziauskas et al. | ..... | 604/22 |
| 6,322,557 B1 | * | 11/2001 | Nikolaevich et al. | ..... | 606/6 |
| 6,544,254 B1 | * | 4/2003 | Bath | ..................... | 606/6 |

* cited by examiner

*Primary Examiner*—Linda C. M. Dvorak
*Assistant Examiner*—Ahmed Farah
(74) *Attorney, Agent, or Firm*—Walter A. Hackler; Peter Jon Gluck

(57) ABSTRACT

Apparatus for the removal of lens tissue includes a first handpiece having a laser emitting probe sized for insertion into a lens capsule and radiating a lens therein. The laser emitting probe includes a lumen for introducing irrigation fluid into the lens capsule. A second handpiece includes a vibrated needle for insertion into the lens capsule and emulsifying laser eradiated lens tissue. The vibrated needle includes a lumen therethrough for aspiration of emulsified lens tissue and irrigation fluid.

4 Claims, 1 Drawing Sheet

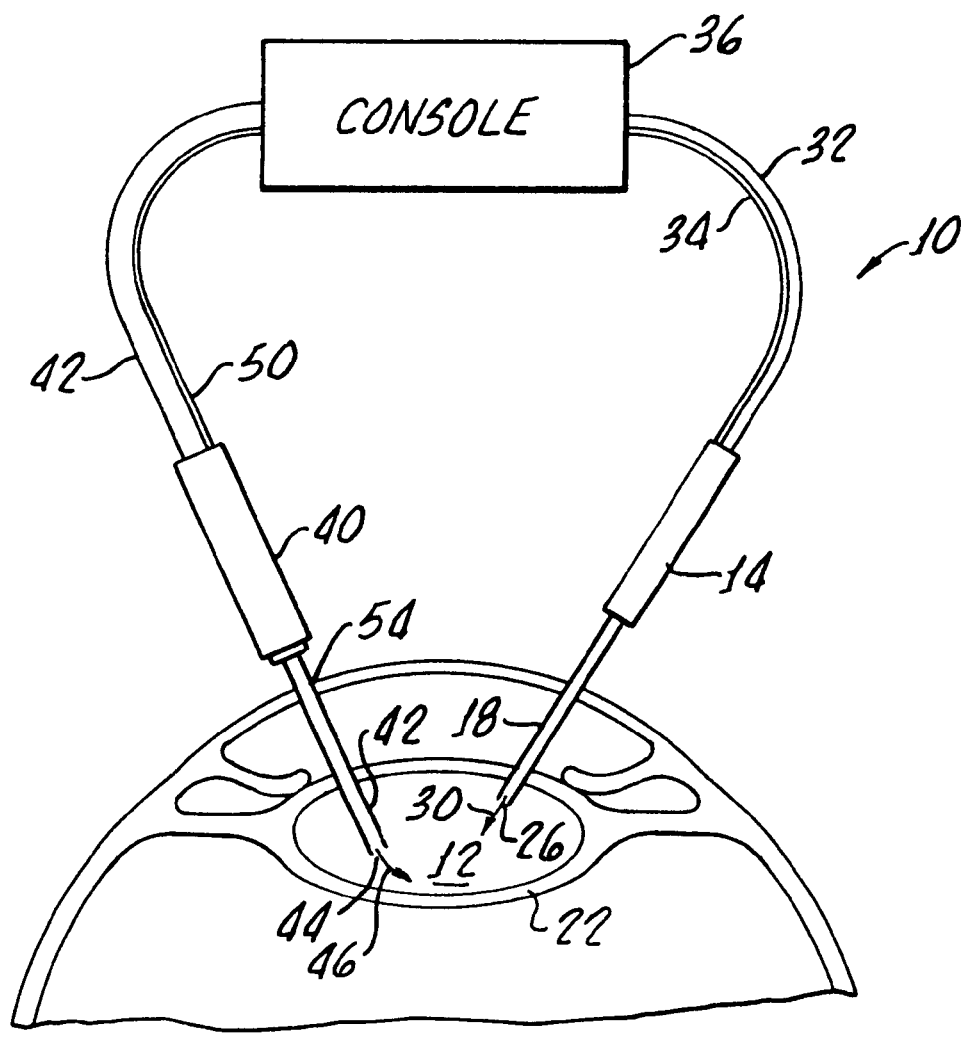

CATARACT EXTRACTION APPARATUS AND METHOD

The present invention generally relates to apparatus and method for extracting cataract tissue and more particularly is directed to combined use of vibrational and laser energy to effect cataract removal.

An eye generally includes an anterior chamber and a posterior chamber separated by a lens contained in a lens capsule. The lens functions to focus incoming light onto a retina disposed on a rear wall of the posterior chamber.

Cataracts cause the lens of an eye to become clouded, which interferes with proper transmission and focusing of light on the retina. A common practice to alleviate this condition is by surgically removing the cataractic lens and replacing it with an artificial intraocular lens.

Early lens removal was effected through manual extraction which required a wound of about 12 mm in length. This large opening can result in corneal or sclera tissue damage.

Externally applied laser radiation has been used to soften a cataract lens before manual extraction therefor. See U.S. Pat. Nos. 4,825,865, 5,057,098, 5,112,339, 5,139,504 and 5,403,307. Such manual extraction requires large entry wounds as hereinabove noted.

Phacoemulsification, on the other hand, enables the removal of a cataractic lens through a much smaller incision, for example between about 2.5 to about 4 mm. In this procedure, a needle is inserted through the incision into a lens capsule and the needle is ultrasonically vibrated to mechanically emulsify the lens. Once fragmented, or emulsified, the lens material is aspirated through a lumen through the phacoemulsification needle.

While emulsifying the lens and aspirating lens fragments, a simultaneous flow of irrigation fluid into the lens capsule is provided around the needle through an annulus established by a sleeve concentrically disposed over the needle. This flow of liquid into the eye is necessary to prevent collapse of the anterior chamber of the eye during aspiration. In addition, the irrigation fluid cools the needle in order to prevent any thermal damage of the corneal or scleral tissue. While the sleeve surrounding a phacoemulsification needle provides the important function of establishing an annulus for introducing irrigation fluid into the lens capsule and also enlarges the overall diameter of the sleeve needle for which an incision must be made.

In addition, when irrigation fluid is introduced proximate the emulsifying needle tip, the immediate area in front of the needle is roiled. This occurs because of the counter-current flow of fluid being aspirated by the needle itself and the irrigation fluid being introduced over the surface of the needle. Needle vibration causes a cloud of debris which is roiled by the incoming infusion fluid which lessons the physicians visual acuity of the end of the needle which can slow the procedure.

The present invention provides for the combined use of laser and vibrational energy to remove cataractic lens tissue and overcomes the drawbacks of a sleeved phacoemulsification needle.

SUMMARY OF THE INVENTION

Apparatus in accordance with the present invention for the removal of lens tissue generally includes a first handpiece including a laser emitting probe sized for insertion into a lens capsule and radiating lens tissue therein. In addition, the laser emitting probe includes a lumen for introducing an irrigation fluid into the lens capsule.

In combination therewith, a second handpiece is provided which includes a vibrated needle for insertion into the lens capsule and emulsifying lens tissue that has been softened, or fractured, by the laser radiation. The vibrated needle includes a lumen therethrough for aspiration of the emulsified lens tissue and irrigation fluid.

A control console is provided and interconnected with both first and second handpieces for controlling irrigation and aspiration rates and enabling simultaneous sequential operation of the laser emitting probe and the vibrated needle. In this manner, particularly hard or lens portions, that are resistant to emulsification, may be preconditioned for emulsification by laser radiation. The softening of lens tissue by laser is well known as set forth in the hereinabove referenced U.S. Patents.

Because irrigation fluid is not simultaneously introduced proximate the vibrating needle, as is the case in prior art devices, no disturbance or churning of fluid occur which may provide for a "milky cloud" at the end of the needle which can tend to lessen visual acuity, which in turn, may interfere with the accuracy of the phacoemulsification by a physician.

Preferably the second handpiece includes a transducer for driving the vibrating needle at ultrasonic frequencies and the laser emitting probe comprises fiber optics with a irrigation lumen therethrough.

A method in accordance with the present invention for removing lens tissue from a lens capsule generally includes the steps of inserting a laser emitting probe having an irrigation lumen into the lens capsule along with a vibratable needle having an aspiration lumen.

Irrigation fluid is introduced into the lens capsule and the lens is softened or fractured by exposure to laser energy from the laser emitting probe.

The needle is vibrated to emulsify the lens tissue which is thereafter aspirated along with the irrigation fluid through an aspiration lumen in the vibratable needle.

The lens tissue may be exposed to laser radiation and emulsified simultaneously or the laser exposure may be intermittent and in a sequential manner. That is, the tissue may first be repeatedly exposed to laser radiation and thereafter emulsified.

BRIEF DESCRIPTION OF THE DRAWING

The advantages and features of the present invention will be better understood by the following description when considered in conjunction with the accompanying drawing in which:

FIG. 1 is a diagram of apparatus in accordance with the present invention generally showing a first handpiece for inserting a laser emitting probe into a lens capsule along with introducing an irrigation fluid into the lens capsule along with a second handpiece for inserting a vibratable needle into the lens capsule for emulsification of lens tissue and aspiration of emulsified tissue and irrigation fluid.

DETAILED DESCRIPTION

With reference to FIG. 1 there is shown apparatus 10 for the removal of lens tissue 12. The apparatus 10 generally includes a first handpiece 14 which includes a laser emitting probe 18 for insertion into a lens capsule 22 for radiating the lens tissue 12. The handpiece 14 may include any suitable laser, such as, a Er:YAG laser for providing laser energy to the probe 18 which includes fiber optics for transmitting the laser energy into the lens capsule 22 and lens 12. A lumen 26 through the probe 18 is provided for introducing an irrigation fluid, indicated by the arrow 30, into the lens capsule 22. Power and irrigation fluid are provided to the handpiece 14 through lines 32, 34 connected to a control console 36. The control counsel 36 may be of any suitable type, such as for example, one manufactured by Allergan, Inc. under the trade name Sovereign®.

A second handpiece 40 includes a vibrated needle 42 for emulsifying lens tissue 12. Any suitable handpiece may be utilized, such as for example, one sold by Allergan, Inc. under the trade name Sovereign®. The handpiece 40 is interconnected to the console 36 and controlled thereby through a power line 42. A lumen 44 through the needle 42 is provided for aspiration of emulsified lens tissue 12 and irrigation fluid as indicated by the arrow 46. Vacuum is provided by the console through an aspiration line 50 interconnecting the handpiece 40, needle lumen 44 to the console 36.

In operation, the laser emitting probe is utilized to soften, or fracture selected portion of the lens which are thereafter emulsified by the needle 42 and aspirated through the lumen 44 and line 50. The laser probe 18 and emulsifying needle 42 may be operated simultaneously to effect lens removal or in a sequential manner in which the lens 12 is preferably radiated by laser light and thereafter emulsified by the vibrating needle 42.

It should also be noted that since the needle 42 does not include a conventional sleeve (not shown) a smaller incision or wound 54 is enabled. The wound size may be a small as 1.25 mm which is to be compared with conventional sleeve needle (not shown) which require a slit or wound opening (not shown) of about 2½ to 3 mm.

A combined use of the laser emitting probe 18 emulsifying needle 42 increases the efficiency of lens removal, and is particularly useful in cases in which the lens is of sufficient hardness such that laser energy alone would not efficiently extract the cataract. The laser, in combination with ultrasonic energy, would result in a lower total energy required to extract the cataract. This may also reduce the likelihood of adverse events such as would burns. In addition, smaller incisions may be used for cataract extraction.

Although there has been hereinabove described an apparatus and method for the removal of lens tissue in accordance with the present invention for the purpose of illustrating the manner in which the invention may be used to advantage, it should be appreciated that the invention is not limited thereto. Accordingly, any and all modifications, variations, or equivalent arrangements which may occur to those skilled in the art should be considered to be within the scope of the invention as defined in the appended claims.

What is claimed is:

1. A method for removing lens tissue from a lens capsule, said method comprising:

inserting a laser emitting probe having an irrigation lumen into said lens capsule;

inserting a vibratable needle having an aspiration lumen into said lens capsule;

introducing irrigation fluid into said lens capsule through said irrigation lumen;

softening said lens tissue by exposure to laser energy from said laser emitting probe;

vibrating the needle to emulsify softened lens tissue;

controlling operation of the laser emitting probe and vibratable needle simultaneously and sequentially in order to effect emulsification of the lens tissue; and aspirating emulsified lens tissue and irrigation fluid from said lens capsule through said aspiration lumen.

2. The method according to claim 1 wherein the needle is vibrated ultrasonically.

3. A method for removing lens tissue from a lens capsule, said method comprising:

inserting a laser emitting probe having an irrigation lumen into said lens capsule;

inserting a vibratable needle having an aspiration lumen into said lens capsule;

introduction irrigation fluid into said lens capsule through said irrigation lumen;

fracturing said lens tissue by exposure to laser energy from said laser emitting probe;

vibrating the needle to emulsify fractured lens tissue;

controlling the fracturing of said lens tissue and emulsification of fractured lens tissue simultaneously and sequentially in order to effect emulsification of the lens tissue; and aspirating emulsified lens tissue and irrigation fluid from said lens capsule through said aspiration lumen.

4. The method according to claim 3 wherein the needle is vibrated ultrasonically.

* * * * *